(12) United States Patent
Salvi et al.

(10) Patent No.: US 8,324,411 B2
(45) Date of Patent: Dec. 4, 2012

(54) PROCESS FOR THE PREPARATION OF DIACEREIN

(75) Inventors: Annibale Salvi, Milan (IT); Antonio Nardi, Segrate (IT); Stefano Maiorana, Milan (IT); Mara Sada, Segrate (IT)

(73) Assignee: Laboratorio Chimico Internazionale S.p.A., Milan (IT)

( * ) Notice: Subject to any disclaimer, the term of this patent is extended or adjusted under 35 U.S.C. 154(b) by 99 days.

(21) Appl. No.: 12/811,423

(22) PCT Filed: Dec. 19, 2008

(86) PCT No.: PCT/IB2008/003555
§ 371 (c)(1),
(2), (4) Date: Sep. 28, 2010

(87) PCT Pub. No.: WO2009/090483
PCT Pub. Date: Jul. 23, 2009

(65) Prior Publication Data
US 2011/0015269 A1    Jan. 20, 2011

(30) Foreign Application Priority Data
Jan. 4, 2008 (IT) .............................. MI2008A0011

(51) Int. Cl.
*C07C 49/593* (2006.01)
(52) U.S. Cl. ...................................................... 552/262
(58) Field of Classification Search ................... 552/262
See application file for complete search history.

(56) References Cited

U.S. PATENT DOCUMENTS
5,652,265 A     7/1997  Vittori et al.
2006/0135797 A1*  6/2006  Maggi .......................... 552/262

FOREIGN PATENT DOCUMENTS
EP  0 928 781       7/1999
WO  WO2006/051400  * 5/2006
WO  WO 2006/051400   5/2006

OTHER PUBLICATIONS

Carney et al. CAS: 127: 13413, 1997.*
International Search Report for PCT/IB2008/003555, mailed Jun. 16, 2009.
Written Opinion of the International Searching Authority for PCT/IB2008/003555, mailed Jun. 16, 2009.
Mangzhu, Z. et al., "Oxidation of Primary Alcohols to Carboxylic Acids with Sodium Chlorite Catalyzed by TEMPO and Bleach", Journal of Organic Chemistry, vol. 64, No. 7, (Apr. 2, 1999), pp. 2564-2566.

* cited by examiner

*Primary Examiner* — Rei-tsang Shiao
(74) *Attorney, Agent, or Firm* — Nixon & Vanderhye P.C.

(57) ABSTRACT

The invention concerns a new process for the preparation of high purity diacerein, by oxidization of the protected aloe-emodin in the presence of an oxidizing system and radical catalyst and subsequent substitution of the protector groups with acetyl groups.

16 Claims, No Drawings

PROCESS FOR THE PREPARATION OF DIACEREIN

This application is the U.S. national phase of International Application No. PCT/IB2008/003555 filed 19 Dec. 2008, which designated the U.S. and claims priority to IT Application No. MI2008A000011 filed 4 Jan. 2008, the entire contents of each of which are hereby incorporated by reference.

SUMMARY OF THE INVENTION

The present invention concerns a new process for the preparation of diacerein, in particular a new synthetic method by oxidisation with radical catalysis which produces diacerein with a high level of purity and excellent yields.

PRIOR ART

Diacerein (4,5-bis(acetyloxy)-9,10-dihydro-9,10-dioxo-2-anthracene carboxylic acid) is a molecule with antiarthritic activity, which has been used in therapy for a very long time.

Many syntheses of diacerein are known, the majority of which use aloin as a starting product which, after acetylation of the hydroxylic groups, is oxidised with chromic anhydride in acetic acid. The diacerein thus obtained requires many purification stages in order to eliminate the residues of chromium and the reaction by-products (see for example EP 0 636 602, WO 98/56750, WO 01/96276, US 2006/0135797, US 2007/0037992). However, the repeated purifications, which are labour-intensive in industrial terms, are not sufficient to eliminate the residues of chromium and the by-products, in particular the aloe-emodin and its acetyl derivatives, which are therefore found as impurities in the end product.

WO 2006/051400 describes a process for the preparation of diacerein which uses sodium nitrite in sulphuric acid instead of the chromic anhydride/acetic acid oxidising system. Said process is extremely exothermic and hence cannot be controlled in large-scale production; furthermore the volumes of solvent necessary for the reactions are excessive and the yields are very low. Also said process is therefore not suitable for industrial production.

OBJECTS OF THE INVENTION

The object of the present invention is to provide a process for the preparation of diacerein which overcomes the drawbacks of the prior art and allows the production of diacerein with a high level of purity and high yields, via a safe and industrially feasible synthesis.

In fact, it has surprisingly been found that the alpha carbon to the hydroxymethyl chain of the aloe-emodin can be oxidised with an oxidising agent more suitable for industrial use than those used in the known art.

DESCRIPTION OF THE INVENTION

Thus, according to one of its aspects, the invention concerns a process for the preparation of 4,5-bis(acetyloxy)-9,10-dihydro-9,10-dioxo-2-anthracene carboxylic acid (below also diacerein) of formula (I)

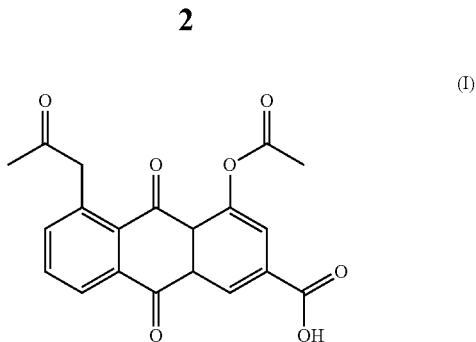

and its salts, which comprises:
a) reacting a protected aloe-emodin of formula (II)

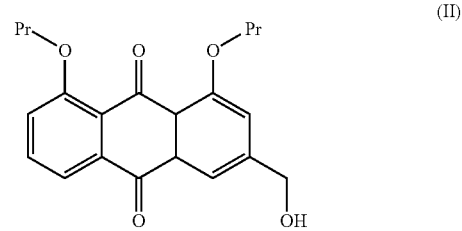

in which Pr is a protector group non-hydrolysable in an aqueous environment, with an oxidising system which comprises the radical 2,2,6,6-tetramethyl-1-piperidinyl-N-oxyl of formula (III):

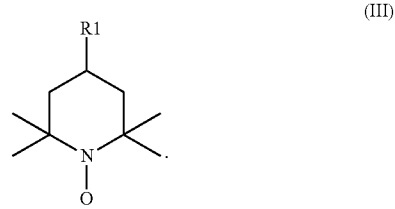

where $R_1$ is H, OH, O-alkyl or O-alkanoyl, in the presence of an alkaline or alkaline-earth chlorite and an alkaline or alkaline-earth hypochlorite, in an appropriate solvent, to give the compound of formula (IV)

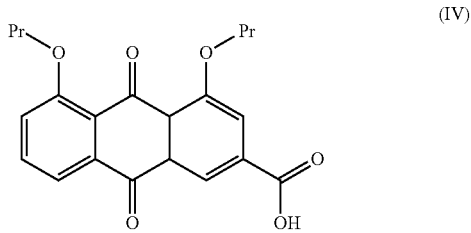

b) replacing the Pr protector groups with acetyl groups and, if desired, isolating and purifying the diacerein thus obtained.

According to the present invention, the Pr groups are protector groups which are not hydrolysable in an aqueous environment and are compatible with the oxidisation reaction, preferably protector groups which can be cleaved with a Lewis acid, for example with an acetic anhydride/$FeCl_3$ system.

Suitable protector groups are for example the benzyl or substituted benzyl groups.

The terms alkaline or alkaline-earth chlorite/hypochlorite indicate a chlorite/hypochlorite salt with an alkaline or alkaline-earth metal. A particularly preferred metal is sodium.

The radical oxidising system of formula (III) with alkaline or alkaline-earth chlorite and alkaline or alkaline-earth hypochlorite is known in the art.

A preferred radical of formula (III) is the radical 2,2,6,6-tetramethyl-1-piperidinyl-N-oxyl (hereinafter also TEMPO).

The radical of formula (III), advantageously the TEMPO radical, is generally used in quantities that vary from 4 to 10% in moles, preferably 6 to 8% in moles with respect to the moles of compound to be oxidised.

The alkaline or alkaline-earth chlorite is generally used in quantities that vary from 160 to 250%, preferably from 200 to 220% in moles with respect to the moles of compound to be oxidised.

The alkaline or alkaline-earth sodium hypochlorite is generally used in quantities that vary from 2.0 to 8%, preferably from 5 to 6% in moles with respect to the moles of compound to be oxidised.

The solvent used in the oxidisation reaction is an inert solvent, chosen for example from acetonitrile; linear or cyclic ethers, such as tetrahydrofuran, dioxane, diethyl ether, dimethyl ether, methyl tert-butyl ether, diglyme, triglyme; tertiary alcohols; benzene; toluene; alkanes such as hexane, pentane; halogenated solvents such as chloroform; carbon tetrachloride; and their mixtures.

A particularly preferred solvent is acetonitrile.

The oxidisation reaction is advantageously carried out in two phases: firstly the starting compound of formula (II) is reacted, in the reaction solvent, with the radical of formula (III) and alkaline or alkaline-earth chlorite, advantageously at a temperature between the room temperature and 50° C., preferably around 30-40° C., for example at approximately 35° C.

In the second phase the sodium hypochlorite is added and the mixture is reacted at a temperature advantageously between the room temperature and the reflux temperature, preferably around 50-80° C., for example at approximately 60-65° C.

According to a particularly advantageous embodiment, the oxidisation reaction is carried out in the presence of a buffer system, for example a phosphate buffer system at pH 6-7 (alkaline or alkaline-earth dihydrogen phosphate/sodium hydrogen phosphate).

The oxidisation reaction is complete in a few hours. Normally 2 to 5 hours are sufficient for all the starting product to be oxidised; a person skilled in the art can in any case monitor the course of the reaction by means of the known techniques.

According to a preferred embodiment of the invention, the product of formula (IV) obtained from the oxidisation reaction (a) is purified, for example, by repeated extraction with an appropriate solvent of an aqueous/organic solution of one of its salts.

According to a particularly preferred embodiment, the product of formula (IV), for example the product of formula (IV) wherein the Pr groups which are benzyl or substituted benzyl groups, obtained from the oxidisation reaction (a) is purified by dissolution in a mixture of water and dimethyl formamide, in the presence of an amine, for example a tertiary amine such as triethyl amine; after repeated extraction of the aqueous/organic phase, for example with ethyl acetate, an acid is added to the aqueous/organic phase, for example hydrochloric acid, and the precipitate that forms is isolated.

The compound of formula (IV) where Pr is benzyl, i.e. 1,8-dibenzyl oxyanthraquinone-3-carboxylic acid (dibenzyl-rhein) which can be obtained from step (a), is an intermediate product, described in detail and characterised in the following experimental section, and represents a further subject-matter of the present invention.

The product of formula (IV) can be converted into diacerein also by means of one single reaction, by treatment with an acetylating agent, for example acetic anhydride, in the presence of an appropriate catalyst, for example a Lewis acid, advantageously iron trichloride, preferably anhydrous. In this way the Pr groups are removed and the acetyl groups are introduced by one single reaction.

Thus, according to a particularly preferred embodiment, the invention concerns a process for the preparation of diacerein which comprises reacting a compound of formula (II), in which Pr is a benzyl or protected benzyl group, with a radical of formula (III) in which $R_1$ is H, in the presence of alkaline or alkaline-earth chlorite, advantageously sodium chlorite, and alkaline or alkaline-earth hypochlorite, advantageously sodium hypochlorite, in an appropriate solvent, and subsequently reacting a compound of formula (IV) thus obtained with acetic anhydride in the presence of anhydrous iron trichloride.

The diacerein thus obtained can be used as is or, if desired or necessary, further purified according to the methods known to a person skilled in the art. In the synthesis there are no reagents containing chromium and this results in the important advantage of obtaining a chromium-free end compound. To confirm this, analyses were performed on the compound of formula (I) which demonstrated that the chromium content is below the traceability limit of the equipment used (<1 ppm).

With the process of the invention, diacerein is obtained which does not contain chromium (<1 ppm) and which has a content of aloe emodin (or its acetyl derivatives) not exceeding 2 ppm. Said compound represents a further subject of the invention.

The present invention also concerns the pharmaceutical compositions comprising diacerein which does not contain chromium, for example where the chromium is below the traceability limit (<1 ppm).

The present invention furthermore concerns the pharmaceutical compositions comprising diacerein which has a content of aloe emodin (or its acetyl derivatives) not exceeding 2 ppm, advantageously between 2 ppm and 0.1 ppm, for example between 2 ppm and 0.5 ppm, or below the traceability limit.

According to another of its aspects, the invention also concerns the use of diacerein which does not containing chromium (<1 ppm) and with a content of aloe emodin (or its acetyl derivatives) not exceeding 2 ppm (advantageously between 2 ppm and 0.1 ppm, for example between 2 ppm and 0.5 ppm, or below the traceability limit) for the preparation of a pharmaceutical composition, advantageously for a pharmaceutical composition with antiarthritic activity.

Preferred embodiments of the invention are described in detail in the experimental part of the present invention.

EXPERIMENTAL SECTION

Example 1

Preparation of
1,8-dibenzyloxy-3-(hydroxymethyl)anthraquinone
(dibenzyl aloe-emodin)

483 g (3.5 moles) of potassium carbonate, 16 g (0.1 moles) of potassium iodide and 16 g (0.05 moles) of tetrabutylammonium bromide are added to a solution of 270 g (1 mole) of 1,8-dihydroxy-3-(hydroxymethyl)anthraquinone (aloe-emodin) in 3500 ml of DMF at 60° C.; the reaction mixture is heated at 80° C. for 1 h. It is cooled to 50° C. and 443 g (3.5 moles) of benzyl chloride are added dropwise in approximately one hour. At the end of the dripping, the reaction mixture is brought back to 80° C. and left at that temperature under stirring for 45-60 minutes. It is then cooled to 50° C. and 200 ml of methyl alcohol are added. It is cooled to 20-25° C. and the inorganic salts are removed by filtering. The organic solvent is distilled at 60-70° C. at reduced pressure and the residue is dissolved in 3200 ml of tetrahydrofuran at 60° C. Maintaining the temperature at 50-60° C., the organic phase is washed twice with 1200 ml of 2.5 molar aqueous sodium hydroxide and once with 1000 ml of a saturated solution of sodium chloride in water. The organic phase is concentrated at reduced pressure at 60° C. and the residue is recovered with 2700 ml of ethyl acetate. The suspension thus obtained is concentrated to approximately ⅓ of the initial volume by distillation of the solvent at reduced pressure. It is gradually cooled to 0-4° C. and kept at that temperature for 1 hour. The solid is filtered and washed with ethyl acetate (100 ml×2). The damp product is dried at 45° C. at reduced pressure for 12-14 hours, providing 334 g (yield 74%) of dibenzyl aloe-emodin having a purity of 98% (HPLC).

melting point: 170-171° C.
IR cm$^{-1}$: 1655, 1612, 1232

Example 2

Synthesis of
1,8-dibenzyloxyanthraquinone-3-carboxylic acid
(dibenzylrhein)

10 g (0.06 moles) of radical 2,2,6,6-tetramethyl-1-piperidinyl-oxyl (TEMPO) and 1160 ml of an aqueous solution of 120 g (1 mole) of sodium dihydrogen phosphate and 180 g (1 mole) of disodium hydrogen phosphate are added in sequence to a suspension of 333 g (0.74 moles) of 1,8-dibenzyloxy-3-(hydroxymethyl)anthraquinone in 1660 ml of acetonitrile. The reaction mixture is heated to 35° C. and a solution of 167 g (1.5 moles) of sodium chlorite 80% in 513 ml of water is added dropwise in 40-50 minutes, maintaining the temperature around 35-40° C. 20 ml of aqueous sodium hypochlorite 10-12% are then dripped in and the reaction is heated to 60-65° C. for three hours. It is cooled to room temperature and 1400 ml of water are added. Phosphoric acid 85% is dripped in until reaching a pH of 2.8-3.2. The solid obtained is filtered and washed with water (350 ml×2). The damp product is dried at 50° C. at reduced pressure for 14-16 hours, providing 337 g (yield 98%) of crude dibenzylrhein.

Example 3

Purification of
1,8-dibenzyloxyanthraquinone-3-carboxylic acid
(dibenzylrhein)

337 g (0.72 moles) of crude 1,8-dibenzyloxyanthraquinone-3-carboxylic acid are dissolved in a solution of 134 ml of triethylamine in 900 ml of dimethylformamide DMF and 1800 ml of ethyl acetate, heating to 60° C. for 20-30 min. Any undissolved elements are removed by hot filtering and 2700 ml of water are added. The organic phase is separated and the aqueous phase is washed 6 times with 800 ml of ethyl acetate each time, maintaining the temperature at 60° C. The organic phase is cooled to room temperature and acidified with hydrochloric acid 33% until pH 2 is reached; the suspension thus obtained is cooled to 0-5° C. for approximately 1 hour. The product is filtered, washing it thoroughly with water (1200 ml) and then with 200 ml of acetonitrile. After drying at 50° C. at reduced pressure for 14-16 hours, 256 g of dibenzylrhein are obtained with a yield of 76%.

melting point: 250-251° C.
IR cm$^{-1}$: 1666, 1621, 1587, 1524

Example 4

Synthesis of 1,8-diacetoxy-3-carboxyanthraquinone
(diacerein)

45 g (0.28 moles) of anhydrous iron trichloride are added in portions to a suspension of 255 g (0.55 moles) of 1,8-dibenzyloxyanthraquinone-3-carboxylic acid in 1300 ml of acetic anhydride. The reaction mixture is heated to 65° C. for one hour and thirty minutes. It is gradually cooled to 2-4° C. and maintained at that temperature for 1 hour. The solid obtained is filtered and washed with 150 ml of acetic anhydride and then with 400 ml of ethyl acetate. The damp product is dried at 50° C. at reduced pressure for 14-16 hours, providing 186 g of crude diacerein (yield 92%). The crude diacerein is purified according to the known techniques.

$^1$H NMR (d6-DMSO) δ: 2.4 (6H, s); 7.6 (1H, dd); 7.9 (1H, t); 8.0 (1H, d); 8.1 (1H, dd); 8.5 (1H, d).
IR cm$^{-1}$: 1763, 1729, 1655, 1619, 1591, 1183.
Chromium: not detectable (<1 ppm)
Genotoxic impurities (aloe emodin and acetyl derivatives) ≦2 ppm.

The invention claimed is:
1. A process for the preparation of 4,5-bis(acetyloxy)-9,10-dihydro-9,10-dioxo-2-anthracene carboxylic acid of formula (I)

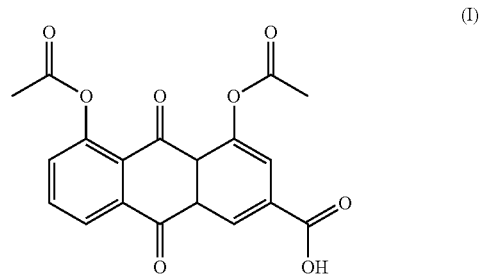

and its salts, which comprises:
a) reacting a protected aloe-emodin of formula (II)

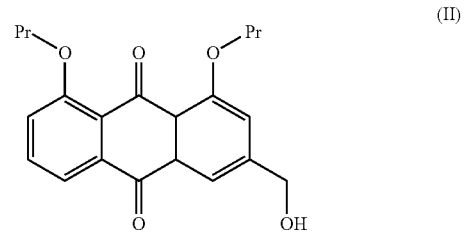

in which Pr is a benzyl or substituted benzyl group not hydrolysable in an aqueous environment, with an oxidising system which comprises the radical 2,2,6,6-tetramethyl-1-piperidinyl-N-oxyl of formula (III):

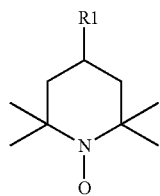

where R₁ is chosen from H, OH, O-alkyl and O-alkanoyl, in the presence of an alkaline or alkaline-earth chlorite and an alkaline or alkaline-earth hypochlorite, in an appropriate solvent, to give the compound of formula (IV)

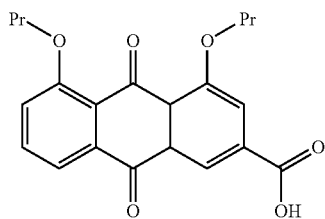

b) replacing the Pr protector groups with acetyl groups and optionally isolating and purifying the compound of formula (I) thus obtained.

2. The process as claimed in claim 1, wherein the Pr groups are as defined in claim 1.

3. The process as claimed in claim 1 wherein the radical of formula (III) is used in quantities that vary from 4 to 10% in moles with respect to the moles of the compound to be oxidised.

4. The process as claimed in claim 1 wherein the alkaline or alkaline-earth chlorite is used in quantities that vary from 160 to 250% in moles with respect to the moles of compound to be oxidised.

5. The process as claimed in claim 1 wherein the alkaline or alkaline-earth hypochlorite is used in quantities which vary from 2 to 8% in moles with respect to the moles of the compound to be oxidised.

6. The process as claimed in claim 1 wherein the radical of formula (III) is used in quantities which vary from 6 to 8% in moles, the alkaline or alkaline-earth chlorite is used in quantities which vary from 200 to 200% and the alkaline or alkaline-earth hypochlorite is used in quantities which vary from 5 to 6% in moles, with respect to the moles of compound to be oxidised.

7. The process as claimed in claim 1 wherein said alkaline or alkaline-earth chlorite is sodium chlorite.

8. The process as claimed in claim 1 wherein said alkaline or alkaline-earth hypochlorite is sodium hypochlorite.

9. The process as claimed in claim 1 wherein the radical of formula (III) is 2,2,6,6-tetramethyl-1-piperidinyl-N-oxyl.

10. The process as claimed in claim 1 wherein said solvent is chosen from acetonitrile, linear or cyclic ethers, tertiary alcohols, benzene, toluene, alkanes, halogenated solvents and their mixtures.

11. The process as claimed in claim 10, wherein said solvent is chosen from acetonitrile, tetrahydrofuran, dioxane, diethyl ether, dimethyl ether, methyl tert-butyl ether, diglyme, triglyme, hexane, pentane, benzene, toluene, chloroform and carbon tetrachloride and their mixtures.

12. The process as claimed in claim 1 wherein the oxidisation reaction is carried out in the presence of a buffer system.

13. The process as claimed in claim 12, wherein said buffer system is a phosphate buffer system (sodium dihydrogen phosphate/sodium hydrogen phosphate).

14. The process as claimed in claim 1 wherein the compound of formula (IV) is purified before the step (b).

15. The process as claimed in claim 1 wherein the step (b) is performed with an acetylating agent/Lewis acid system.

16. The process as claimed in claim 14 wherein said acetylating agent is the acetic anhydride and the Lewis acid is the anhydrous ferric chloride.

* * * * *